US007303906B2

(12) United States Patent
Blattner et al.

(10) Patent No.: US 7,303,906 B2
(45) Date of Patent: Dec. 4, 2007

(54) COMPETENT BACTERIA

(75) Inventors: Frederick R. Blattner, Madison, WI (US); Gyorgy Posfai, Szeged (HU); Christopher D. Herring, Madison, WI (US); Guy Plunkett, III, Madison, WI (US); Jeremy Glasner, Madison, WI (US); Trevor Twose, Madison, WI (US)

(73) Assignees: Wisconsin Alumni Research Foundation, Madison, WI (US); Scarab Genomics, LLC, Madison, WI (US)

( * ) Notice: Subject to any disclaimer, the term of this patent is extended or adjusted under 35 U.S.C. 154(b) by 0 days.

(21) Appl. No.: 10/655,914

(22) Filed: Sep. 5, 2003

(65) Prior Publication Data

US 2005/0032225 A1 Feb. 10, 2005

Related U.S. Application Data

(60) Provisional application No. 60/409,089, filed on Sep. 6, 2002.

(51) Int. Cl.
*C12N 1/20* (2006.01)
*C12N 1/22* (2006.01)

(52) U.S. Cl. .............................. 435/252.8; 435/252.33

(58) Field of Classification Search .................. None
See application file for complete search history.

(56) References Cited

U.S. PATENT DOCUMENTS

| | | | | |
|---|---|---|---|---|
| 4,851,348 A * | 7/1989 | Hanahan | ........................ | 435/6 |
| 4,981,797 A | 1/1991 | Jessee et al. | ............. | 435/252.8 |
| 5,578,464 A | 11/1996 | Lunn et al. | ................ | 435/69.1 |
| 5,747,662 A | 5/1998 | Simmons et al. | .......... | 536/24.1 |
| 5,824,502 A | 10/1998 | Honjo et al. | ............... | 435/69.1 |
| 5,962,327 A | 10/1999 | Dujon et al. | ................ | 435/478 |
| 6,015,709 A | 1/2000 | Natesan | ....................... | 435/366 |
| 6,022,952 A | 2/2000 | Weiner et al. | .............. | 530/350 |
| 6,117,680 A | 9/2000 | Natesan et al. | ............. | 435/455 |
| 6,238,924 B1 | 5/2001 | Dujon et al. | ................ | 435/477 |
| 6,335,178 B1 | 1/2002 | Weiner et al. | .............. | 435/69.1 |
| 6,372,476 B1 | 4/2002 | Belguith et al. | ............ | 435/233 |
| 6,410,273 B1 | 6/2002 | Crouzet et al. | ............. | 435/91.1 |
| 6,509,156 B1 | 1/2003 | Stewart et al. | ................ | 435/6 |
| 6,989,265 B2 | 1/2006 | Blattner et al. | .......... | 435/252.8 |
| 2003/0138937 A1 | 7/2003 | Blattner et al. | ........ | 435/252.33 |

FOREIGN PATENT DOCUMENTS

| | | |
|---|---|---|
| EP | 0177343 | 4/1986 |
| EP | 0 283 7236 | 9/1988 |
| WO | WO 88/05821 | 8/1988 |
| WO | WO 96/14408 | 5/1996 |
| WO | WO 01/27258 | 4/2001 |
| WO | WO 02/14495 | 2/2002 |
| WO | WO 03/048374 | 6/2003 |
| WO | WO 03/070880 | 8/2003 |
| WO | WO 2005/087940 | 9/2005 |

OTHER PUBLICATIONS

Pope et al., Nucleic acids Research, 1996, 24(3):536-537.*
Mersereau et al., Gene 90(1) 149-151, 1990.*
Hengen, Trends in Biochem. Sci., 19:426-427, 1994.*
Hengen Trends in Biochem. Sci., 21:75-76, 1996.*
Wirth et al., Mol. Gen. genet. 216:175-177 (1989).*
GenBank Accession No. AP009048, retrieved Apr. 11, 2007.
Hall, "Activation of the bgl operon by adaptive mutation," *Mol. Biol. Evol.*, 15:1-5, 1998.
Khosla et al., "Expression of Recombinant Proteins in *Escherichia Coli* Using an Oxygen-Responsive Promoter," *Bio/Technology*, 8:554-558, 1990.
Passoth et al., "Analysis of the hypoxia-induced ADH2 promoter of the respiratory yeast *Pichia stipitis* reveals a new mechanism for sensing of oxygen limitation in yeast," *Yeast*, 20:39-51, 2003.
Riggs, "Expression and Purification of Maltose-Binding Protein Fusions," *Current Protocols Mol. Biol.*, 16.6.1-16.6.14, John Wiley and Sons, 1994.
Xu and Tabita, "Positive and negative regulation of sequences upstream of the form II cbb CO2 fixation operon of Rhodobacter sphaeroides," *J. Bacteriol.*, 176:7299-7308, 1994.
Asai et al., "An *Escherichia coli* strain with all chromosomal rRNA operons inactivated: complete exchange of rRNA genes between bacteria," *Proc. Natl. Acad. Sci.*, USA, 96:1971-1976, 1999.
Bass et al., "Mulitcopy suppressors of Prc mutang *Escherichia coli* include two HtrA (DegP) protease homologs (HhoAB), DksA, and a truncated RlpA," *Journal of Bacteriology*, 178(4):1154-1161, 1996.
Beaulieu et al., "Pathogenic behavior of pectinase-defective Erwinia chrysanthemi mutants on different plants," *MPMI*, 6(2):197-202 1993.
Dykstra and Kushner, "Physical characterization of the cloned protease III gene from *Escherichia coli* K-12," *Journal of Bacteriology*, 163(3):1055-1059, 1985.
Eichhorn et al., "Deletion analysis of the *Escherichia coli* taurine and alkanesulfonate transport systems," *Journal of Bacteriology*, 182(10)2687-2695, 2000.
GenBank Accession No. AE014073, retrieved Sep. 27, 2006.
GenBank Accession No. AE014075, retrieved Sep. 27, 2006.
GenBank Accession No. AF348706, retrieved Sep. 27, 2006.
Genbank Accession No. U00096, retrieved Sep. 27, 2006.
Perna et al., "Genome sequence of enterochaemorrhagic *Escherichia coli* 0157:H7," *Nature*, 409:529-533, 2001.
Asai et al., "An *Escherichia coli* strain with all chromosomal rRNA operons inactivated: complete exchange of rRNA genes between bacteria," *Proc. Natl. Acad. Sci.*, USA, 96:1971-1976, 1999.
Bass et al., "Mulitcopy suppressors of Prc mutang *Escherichia coli* include two HtrA (DegP) protease homologs (HhoAB), DksA, and a truncated RlpA," *Journal of Bacteriology*, 178(4):1154-1161. 1996.

(Continued)

*Primary Examiner*—Nancy T. Vogel
(74) *Attorney, Agent, or Firm*—Fulbright & Jaworski, LLP (57) ABSTRACT

The present invention discloses that a bacterium having a genome that is genetically engineered to be at least 10% smaller than the genome of its native parent strain has better transformation competence. Specific *E. coli* strains, having significantly reduced genome sizes, are disclosed which are highly transformation competent. A medium and methodology is taught which enables transformation efficiencies to be increased further.

7 Claims, 4 Drawing Sheets

OTHER PUBLICATIONS

Beaulieu et al., "Pathogenic behavior of pectinase-defective Erwinia chrysanthemi mutants on different plants," *MPMI*, 6(2):197-202, 1993.

Dykstra and Kushner, "Physical characterization of the cloned protease III gene from *Escherichia coli* K-12," *Journal of Bacteriology*, 163(3):1055-1059, 1985.

Eichhorn et al., "Deletion analysis of the *Escherichia coli* taurine and alkanesulfonate transport systems," *Journal of Bacteriology*182(10)2687-2695, 2000.

GenBank Accession No. AE014073.

GenBank Accession No. AE014075.

GenBank Accession No. AF348706.

GenBank Accession No. U00096.

Hengen, "Better competent cells and DNA polymerase contaminants," *Trends in Biochem. Sci.*, 19:426-427, 1994.

Hengen, "Preparing ultra-competent *Escherichia coli*," *Trends in Biochem. Sci.*, 21:75-76, 1996.

Mersereau et al., "Efficient transformation of Agrobacterium tumefaciens by electroporation," *Gene*, 90:149-151, 1990.

Park et al., "MppA, a periplasmic binding protein essential for import of the bacterial cell wall peptide L-Anayl-γ-D-glutamyl-meso-diaminopimelate," *Journal of Bacteriology*, 180(5):1215-1223, 1998.

Pope and Kent, "High efficiency 5 min transformation of *Escherichia coli*," *Nucleic Acids Research*, 24:536-537, 1996.

Posfai et al., "In vivo excision and amplification of large segments of the *Escherichia coli* genome," *Nucleic Acids Research*, 22(12):2392-2398, 1994.

Schutz et al., "Sulfide-quinone reductase from Rhodobacter capsulatus: requirement for growth, periplasmic localization, and extension of gene sequence analysis," *Journal of Bacteriology*, 181(20):6516-6523, 1999.

Shuman, "Active transport of maltose in *Escherichia coli* K12," *J. Biol. Chem.*, 257(10):5455-5461, 1982.

Van Spanning et al., "Isolation and characterization of the moxJ, moxG, moxI, and moxR genes of Paracoccus denitrificans: Inactivation of moxJ, moxG, and moxR and the resultant effect on methylotrophic growth," *Journal of Bacteriology*, 173(21):6948-6961, 1991.

Vellai et al., "Genome economization and a new approach to the species concept in bacteria," *Proc R Soc Lond B*, 266:1953-1958, 1999.

Waller and Sauer, "Characterization of degQ and degS, *Escherichia coli* genes encoding homologs of the DegP protease," *Journal of Bacteriology*, 178(4):1146-1153, 1996.

Wirth et al., "Transformation of various species of gram-negative bacteria belonging to 11 different genera by electroporation," *Mol. Gene.Genet.*, 216:175-177, 1989.

Aristidou et al., "Modification of central metabolic pathway in *Escherichia coli* to reduce acetate accumulation by heterologous expression of the bacillus subtilis acetolactate synthease gene," *Biotechnology and Bioengineering*, 44:944-951, 1994.

Balbas, "Understanding the art of producing protein and non-protein molecules in *E. coli*," *Molec Biotechnol.*, 19:251-267, 2001.

Baneyx, "Recombinant protein expression in *E. coli*," *Curr Opin Biotech*, 10:411-421, 1999.

Bermejo et al., "Expression of clostridium acetobutylicum ATCC 824 genes in *Escherichia coli* for acetone production and acetate detoxification," *Applied and Environmental Microbiology*, 64:1079-1085, 1998.

Berry et al., "Application of metabolic engineering to improve both production and use of biotech indigo," *J Indust Micro & Biotech*, 22:127-133, 2002.

Blattner et al., "The complete genome sequence of *Escherichia coli* K-12," *Science*, 277:1453-1474, 1997.

Blaudeck et al., "Specificity of single peptide recognition in TAT-dependent bacterial protein translocation," *J. Bacteriology*, 183:604-610, 2001.

Chang et al., "Acetate metabolism in a pta mutant of *Escherichia coli* W3110: Importance of maintaining acetyl coenzyme a flux for growth and survival," *Journal of Bacteriology*, 181:6656-6663, 1999.

Chou et al., "Effects of modified glucose uptake using genetic engineering techniques on high-level recombinant protein production in *Escherichia coli* dense cultures," *Biotechnology and Bioengineering* 44:953-960, 1994.

Contiero et al., "Effects of mutations in acetate metabolism on high-cell-density growth of *Eschrichia coli*," *Journal of Industrial Microbiology & Biotechnology*, 24:421-430, 2000.

Court et al., "Genetic engineering using homologous recombination," *Annu Rev Genet*, 36:361-388, 2002.

Danese et al., "Targeting and assembly for periplasmic and outer-membrane proteins in *Escherichia coli*," *Annu Rev Genet*, 32:59-94, 1998.

Database EMBL, "*E.coli* genomic DNA, Kohara clone #421 (55.1-55.5 min.)," Database Accession No. ECD874, 1997.

Datsenko et al., "One-step inactivation of chromosomal genes in *Escherichia coli* K-12 using PCR products," *Proc. Natl. Acad. Sci.*, USA, 97:6640-6649, 2000.

Dedhia et al., "Overproduction of glycogen in *Escherichia coli* blocked in the acetate pathway improved cell growth," *Biotechnology and Bioengineering*, 44:132-139, 1994.

Degryse, "Evaluation of *Escherichia coli* recBC sbcBC mutants for cloning by recombination in vivo," *J. Biotechnology*, 39:181-187, 1995.

DeLisa et al., "Quorum sensing via AI-2 communicates the metabolic burden associated with heterologous protein production in *E. coli*," *Biotech Bioeng*, 75(4):439-450, 2001.

Diaz-Ricci et al., "Effects of alteration of the acetic acid synthesis pathway on the fermentation pattern of *Escherichia coli*," *Biotechnology and Bioengineering*, 38:1318-1324, 1991.

Farmer et al., "Reduction of aerobic acetate production by *Escherichia coli*," *Applied and Environmental Microbiology*, 63:3205-3210, 1997.

Fekkes et al., "Protein targeting to the bacterial cytoplasmic membrane," *Microbiol. Mol. Biol. Rev.*, 63:161-193, 1999.

Gill et al., "A comparative study of global stress gene regulation in response to overexpression of recombinant proteins in *E. coli*," *Metabolic Engineering*, 2:178-189, 2000.

Hahm D H et al., "Characterization and evaluation of a pta (phoshotransacetylase) negative mutant of *Escherichia coli* HB101 as production host of foreign lipase," *Applied Microbiology and Biotechnology*, 42:100-107, 1994.

Hanahan et al., "Studies on transformation of *Escherichia coli* with plasmids," *J. Mol. Biol.*, 166(4):557-580, 1983.

Hannig, "Strategies for optimizing heterologous protein expression in *Escherichia coli*," *Trends Biotechnol.*, 16(2):54-60. 1998.

Hayashi et al., "Construction of a genetic linkage map of the model legume Lotus japonicus using an intraspecific F2 population," *DNA Research*, 8:11-22, 2001.

Hockney, "Recent developments in heterologous protein production in *Escherichia coli*," *Trends Biotechnol.*, 12(11):456-632, 1994.

Holms, "Flux analysis and control of the central metabolic pathways in *Escherichia coli*," *FEMS Microbiology Reviews*, 19:85-116, 1996.

Holms, "The central metabolic pathways of *Escherichia coli*: relationship between flux and control at a branch point, efficiency of conversion to biomass, and excretion of acetate," *Current Topics in Cellular Regulation*, 28:69-105, 1986.

Hynds et al., "The sec-independent twin-arginine translocation system can transport both tightly folded and malfolded proteins across the thylakoid membrane," *J. Biol. Chem.*, 273:34868-34874, 1998.

Kakuda et al., "Construction of Pta-Ack pathway deletion mutants of *Escherichia coli* and characteristic growth profiles of the mutants in a rich medium," *Bioscience Biotechnology Biochemistry*, 58:2232-2235, 1994.

Kitamura, "DNA sequence changes in mutations in the ton B gene on the chromosome of *Escherichia coli* K-12: insertion elements dominate the spontaneous spectra,," *Jpn J. Genet*, 70:35-46, 1995.

Kolisnychenko et al., "Engineering a reduced *Escherichia coli* genome," *Genome Research*, 12:640-647, 2002.

Koob et al., "Minimizing the genome of *Escherichia coli*," *Ann NY Acad Science*, 745:1-3, 1994.

Koonin, "How many genes can make a cell: the minimal-gene-set concept," *Ann Rev Genome Hum Genet*, 1:99-116, 2000.

Lee, "High cell-density culture of *Escherichia coli*," *TIBTECH*, 14:98-103, 1996.

Murphy, "Use of bacteriophage λ recombination functions to promote gene replacement in *Escherichia coli*" *J. Bacteriol.*, 180:2063-2071, 1998.

Muyrers et al., "Rapid modification of bacterial artificial chromosomes by ET-recombination," *Nucleic Acids Research*, 27:1555-1557, 1999.

Neidhardt et al., "Culture medium for Enterobacteria," *J. Bacteriol.*, 119:736-747, 1974.

Oliner et al., "In vivo cloning of PCR products in *E. coli*," *Nucleic Acids Research*, 2(22):5192-5197, 1993.

Otto et al., "Surface sensing and adhesion of *E. coli* controlled by the Cpx-signaling pathway," *Proc. Natl. Acad. Sci.*, USA, 99(4):2287-2292, 2002.

Perna et al., "The genomes of *Escherichia coli* K-12 and pathogenic *E. coli*," *Pathogenic E. coli Paradigm for Bacterial Pathogensis*, M.S. Donnenberg, Editor, Academmic Press, 2002.

Pfeifer et al., "Biosynthesis of complex polyketides in metabolically engineered strain of *E. coli*," *Science* 291:1790-1792, 2001.

Ponce E., "Effect of growth rate reduction and genetic modifications of acetate accumulation and biomass yields in *Escherichia coli*," *Biotechnology and Bioengineering*, 87:775-780, 1999.

Posfai et al., "Markerless gene replacement in *Escherichia coli* stimulated by a double-strand break in the chromosome," *Nucleic Acids Research*, 27:4409-4415, 1999.

Posfai et al., "Versatile insertion plasmids for targeted genome manipulations in bacteria: isolation, deletion, and rescue of the pathogenicity island LEE of the *Escherichia coli* O157:H7 genome," *J. Bacteriol.*, 179:4426-4428, 1997.

Pugsley, "The complete general secretory pathway in gram-negative bacteria," *Microbiol. Rev.*, 57:50-108, 1993.

Reisenberg, "High cell density cultivation of *E. coli* at controlled specific growth rate," *J. Biotech*, 20(1:17-27, 1991.

Ritz et al., "Roles of thiol redox pathways in bacteria," *Annu Rev Microbiol*, 55:21-48, 2001.

Sang, "High cell-density-culture of *Escherichia coli*," *Trends in Biotechnology*, 14:98-105, 1996.

Santini et al., "A novel sec-independent periplasmic protein translocation pathway in *Escherichia coli*," *EMBO J.*, 17:101-112, 1998.

Sargent et al., "Overlapping functions of components of a bacterial sec-independent protein export pathway," *EMBO J*, 17:3640-3650, 1998.

Schaecter et al., "Introduction," In *Escherichia coli* and *Salmonella*, ed. Neidhart, FC et al., 1-2, ASM Press, Washington, D.C., 1997.

Selinger et al., "RNA expression analysis using a 30 base pair resolution *Escherichia coli* genome array," *Nat Biotechnol*, 18(12):1262-1268, 2000.

Shiloach et al., "Effects of glucose supply strategy on acetate accumulation, by *Escherichia coli* BL21 (lambda-DE3)and *Escherichia coli* JM109," *Biotechnology and Bioengineering*, 49:421-428, 1996.

Shiloach et al., "Growing *E. coli* to high cell density-A historical perspective on method development," *Biotechnology Advances*, 23:345-357, 2005.

Simmons et al., "Translation level is a critical factor for secretion of heterologous proteins in *E. coli*," *Nature*, 14:629-634, 1996.

Sing-Gasson et al., "Maskless fabrication of light-directed oligonucleotide microarrays using a digital micromirror array," *Nat Biotechnol.*, 17(10):974-978, 1999.

Smalley et al., "In search of the minimal *Escherichia coli* genome," *Trends in Microbiology*, 11:6-8, 2003.

Swartz, "Advances in *E. coli* production of therapeutic proteins," *Curr. Opin in Biotech*, 12:195-201, 2001.

Thomas et al., "Export of active green fluorescent protein to the periplasm by the twin-arginine translocase (TAT) pathway in *Escherichia coli*," *Mol Micro*, 39(1):47-53, 2001.

Venkatesan et al., "Complete DNA sequence and analysis of the large virulence plasmid of Shigella flexneir.," *Infection of Immunity*, 3271-3285, 2001.

Weiner et al., "A novel and ubiquitous system for membrane targeting and secretion of cofactor-containing proteins," *Cell*, 93:93-101, 1998.

Welch et al., "Extensive mosaic structure revealed by the complete genome sequence of uropathogenic *Escherichia coli*," *Proc. Natl. Acad. Sci.*, USA, 99(26):17020-17024, 2002.

Yang et al., "Metabolic flux analysis of *Escherichia coli* deficient in the acetate production pathway and expressing the bacillus subtilis acetolactate synthase," *Metabolic Engineering* 1:26-34, 1999.

Yu et al., "An efficient recombination system for chromosome engineering in *Escherichia coli*," *Proc. Natl. Acad. Sci.*, USA, 97:5978-5983, 2000.

Yu et al., "Minimization of the *Escherichia coli* genome using a Tn5-targeted Cre/LoxP excision system," *Nature Biotech*, 20:1018-1023, 2002.f.

Zhang et al., "A new logic for DNA engineering using recombination in *Escherichia coli*," *Nature Genetics*, 20:123-128, 1998.

Zhang et al., "DNA cloning by homologous recombination in *Escherichia coli*," *Nature Biotech.*, 18:1314-1317, 2000.

Zhang et al., "Phage annealing proteins promote oligonucleotide-directed mutagenesis in *Escherichia coli* and mouse ES cells," *BMC Molecular Biology*, 4:1, 2003.

\* cited by examiner

COMPETENT BACTERIA

CROSS-REFERENCE TO RELATED APPLICATIONS

This application claims priority from U.S. provisional patent application Ser. No. 60/409,089 filed Sep. 6, 2002.

STATEMENT REGARDING FEDERALLY SPONSORED RESEARCH OR DEVELOPMENT

This invention was made with United States government support awarded by the following agency:
NIH GM35682
The United States has certain rights in this invention.

BACKGROUND OF THE INVENTION

Bacteria have been used to produce a wide range of commercial products. For example, many *Streptomyces* strains and *Bacillus* strains have been used to produce antibiotics; *Pseudomonas denitrificans* and many *Propionibacterium* strains have been used to produce vitamin B12; some other bacteria have been used to produce vitamin Riboflavin; *Brevibacterium flavum* and *Corynebacterium glutamicum* have been used to produce lysine and glutamic acid, respectively, as food additives; other bacteria have been used to produce other amino acids used as food additives; *Alcaligenes eutrophas* has been used to produce biodegradable microbial plastics; and many *Acetobacter* and *Gluconobacter* strains have been used to produce vinegar. More recently, it has become common for bacteria, such as *Escherichia coli* (*E. coli*), to be genetically engineered and used as host cells for the production of biological reagents, such as proteins and nucleic acids, in laboratory as well as industrial settings. The pharmaceutical industry supports several examples of successful products which are human proteins which are manufactured in *E. coli* cultures cultivated in a fermenter.

It is not an uncommon occurrence for normal bacterial proteins to adversely affect the production or the purification of a desired protein product from an engineered bacteria. For example, when *E. coli* bacteria are used as host cells to generate in large quantity of a desired product encoded by a gene that is introduced into the host cells by a plasmid, certain normal *E. coli* gene products can interfere with the introduction and maintenance of plasmid DNA. More significantly, because of the economies of bacterial culture in making proteins in bacteria, often the cost of purification of a recombinant protein can be more than the cost of production, and some of the natural proteins produced by the bacterial host are sensitive purification problems. Many bacterial strains produce toxins that must be purified away from the target protein being produced and some strains can produce, by coincidence, native proteins that are close in size to the target protein, thereby making size separation not available for the purification process.

Also, however, the genome of a bacteria used in a fermenter to produce a recombinant protein includes many unnecessary genes. A bacteria living in a natural environment has many condition responsive genes to provide mechanisms for surviving difficult environmental conditions of temperature, stress or lack of food source. Bacteria living in a fermentation tank do not have these problems and hence do not require these condition responsive genes. The bacterial host spends metabolic energy each multiplication cycle replicating these genes. Thus the unnecessary genes and the unneeded proteins, produced by a bacterial host used for production of recombinant protein, simply represent lack of efficiencies in the system that could be improved upon.

It is not terribly difficult to make deletions in the genome of a microorganism. One can perform random deletion studies in organisms by simply deleting genomic regions to study what traits of the organism are lost by the deleted genes. It is more difficult, however, to make targeted deletions of specific regions of genomic DNA and more difficult still if one of the objectives of the method is to leave no inserted DNA, here termed a "scar," behind in the organism after the deletion. If regions of inserted DNA, i.e. scars, are left behind after a genomic deletion procedure, those regions can be the locations for unwanted recombination events that could excise from the genome regions that are desirable or engender genome rearrangements. Since in building a series of multiple deletions, scars left behind in previous steps could become artifactual targets for succeeding steps of deletion. This is especially so when the method is used repeatedly to generate a series of deletions from the genome. In other words, the organism becomes by the deletion process genetically unstable if inserted DNA is left behind.

Another attribute of interest in bacterial strains of laboratory and industrial use is what is referred to as transformation competence. It is desirable to introduce exogenous DNA into bacteria in culture so that the bacteria will then stably maintain and reproduce the introduced DNA. Bacterial strains vary in their ability to take up and maintain foreign DNA. This characteristic is their transformation competence.

Certain treatments and culture conditions can affect transformation competence. In general, *E. coli* cells grown in normal growth medium, unlike certain bacilli, do not take up exogenous DNA. It was discovered by Mandel and Higa (*J Mol Biol* 53: 159-162 (1970)) that treatment of *E. coli* with calcium chloride allowed *E. coli* to take up DNA from bacteriophage lambda. Cohen et al (*Proc Nat Acad Sci* 69: 2110 (1972)) observed that *E. coli* could be transformed by this method with plasmid DNA. The state of *E. coli* induced by this treatment, in which they become able to take up DNA became known as "transformation competence" and the cells as "transformation competent cells" or more simply, as "competent cell". Under the Mandel and Higa conditions, the yield of transformants is typically in the region of $10^5$ to $10^6$ transformants per microgram of plasmid DNA.

Since the early observations of Mandel and Higa, many variations of the procedure have been tried in attempts to increase the efficiency of the procedure, in order to maximize the number of transformants per unit input of DNA, and to improve the reproducibility of the procedure notably by Hanahan and coworkers (*J Mol Biol* 166: 557-580). The method of Hanahan is used widely to induce competence. Typically, the yield of transformants using the described method is $10^5$ to $10^8$ transformants per microgram of plasmid DNA.

Generally, researchers have found that the transformation efficiency of competent cells is very variable and it has proven difficult to achieve reproducible results (discussed by Hengen, P. N., *Trends in Biochemical Sciences* 19:426-427 (1994) and *Trends in Biochemical Sciences* 21:75-76 (1996)). It has been found that growth at lower than normal temperature (18° C. to 32° C.) produces higher competence (U.S. Pat. No. 4,981,797 and Inoue H et al, *Gene* 96:23-28 (1990). There is a need for procedures that reproducibly produce competent cells with high transformation efficiency.

Transformation competence is a variable from strain to strain of bacterial hosts. Hanahan found that strain MM294 transformed readily, and developed a derivative strain, DH1, from which many of the strains in use today have been derived. Introduction of the deoR mutation (in strain DH5) appeared to increase the transformation efficiency (Hanahan *Methods in Enzymology* 204:63-113 (1991) and U.S. Pat. No. 4,851,348) though the molecular mechanism of the improvement is still unknown. DH5 has been used extensively for transformation. Commercial strains have also been derived from strain MM294, via strain JM109 and strain AG1. Strain AG1 contains one or more additional uncharacterized mutations that increases transformation efficiency (Bullock et al, *Biotechniques* 5:376 (1987)). The commonly used strain DH10b, which also contains the deoR mutation, was 30 times better than DH1 in transformation with 66 kb plasmid DNA. Its pedigree is different from DH1 and DH5, though they share common ancestors. All of the commonly used strains have undergone numerous mutational and recombinational treatments) and are very distant from wild-type *E. coli* (Bachman, B *Derivation and Genotypes of Some Mutants and Derivatives of E. coli K12*, Vol 2, chapter 133, 2460-2488, in: *Escherichia coli and Salmonella*, Neidhardt, F, editor, $2^{nd}$ Edition, ASM Press, Washington (1996)). There is a need for better characterized strains for transformation work that are nearer to wild-type.

One of the most effective methods of introducing DNA into *E. coli* consists of subjecting the cells to an electric field while they are suspended in a defined medium of low ionic strength containing the DNA it is desired to introduce. This process is known as "electroporation". The transformation efficiency, that is the number of cells that are stably transformed by a unit measure of DNA, may be higher than in competent cells produced by other methods. A high and reproducible efficiency of transformation is desirable because it facilitates or in some cases makes possible cloning of rare and valuable DNA molecules, particularly those available in only small amounts. In particular electroporation is the preferred process for preparing cells for use in cloning bacterial artificial chromosomes ("BACs") and other large DNA vectors commonly used in genomic DNA sequencing.

In order to be competent for transformation using the electroporation method, known as "electroporation competent" or "electro-competent", the *E. coli* cells need to be grown under certain specific conditions and subjected to certain specific treatments. Methods for inducing electroporation competence are described in Dower et al (*Nucleic Acid Research* 16:6127-6145 (1988)), Calvin and Hanahan (*J Bacteriol* 170:2796-2801 (1988)) and U.S. Pat. No. 4,910,140 and U.S. Pat. No. 5,186,800. These publications also discuss the many factors that affect the competence and transformation efficiency of *E. coli*.

However, the methods described in the literature for preparing electroporation competent cells are not ideal. The efficiency of transformation is variable depending upon the strain of bacteria used, the conditions used to grow the bacteria and the conditions used to expose the bacteria to the electric field. In particular, only two growth media have been disclosed for the preparation of competent cells: Luria-Bertani broth, commonly known as 'LB broth' (Miller J H (1972) *Experiments in Molecular Biology*, Cold Spring Harbor Laboratory, New York) and SOB medium, described by Hanahan (*J Mol Biol* 166: 557-580). The composition of LB (per liter of medium) is Bacto Tryptone 10 g, Bacto Yeast Extract 5 g and sodium chloride 10 g. The composition of SOB (per liter of medium) is Tryptone 20 g, Yeast Extract 5 g, sodium chloride 0.5 g, magnesium sulphate 2.4 g and potassium chloride 0.126 g. Neither medium has any additional carbon source, such as glucose or other carbohydrate, or glycerol, or additional pH buffering component such as phosphate or non-metabolisable compounds such as MOPS or Tris. The amino acid compounds in the tryptone and yeast extract serve as both nitrogen and carbon sources.

The stage of the growth cycle at which cells are harvested has been described as critical to success, and there is a narrow window in the cell concentration at harvest, above which, or below which, the transformation efficiency drops off rapidly (Calvin and Hanawalt (1988); Dower et al (1988), supra). In LB medium, the optimal stage of the growth cycle occurs at a cell concentration corresponding to an optical density of 0.6. This is a relatively low cell density, since *E. coli* can grow to cell densities many times higher than this under appropriate fermentation conditions, well known to those trained in the art of fermentation. As a result, the process of preparing electroporation competent cells is wasteful of expensive growth media, fermentor capacity and time, and operator time, compared with a process that could use cells grown to higher cell densities. It also requires more expensive downstream processing equipment and time, since the competent cells need to be recovered from larger volumes of dilute suspension. There is a need for better methods for preparing electroporation competent cells, in particular it would be economically beneficial to have a process in which cells can be grown to much higher cell densities without losing transformation efficiency.

As further evidence of the difficulties scientists face in making competent cells, a market has developed for pre-prepared, frozen competent *E. coli* cells that exhibit a higher, more consistent and reproducible efficiency of transformation. In producing commercial competent cells, manufacturers have resorted to several conditions to improve their processes. U.S. Pat. No. 4,981,797 discloses an improved process operating at temperatures between 18° C. and 32° C., but nevertheless, cells need to be harvested at low cell concentrations. U.S. Pat. No. 6,040,184, U.S. Pat. No. 6,338,965 and WO 0022147 disclose the addition of sorbitol or other sugars to improve the transformation efficiency. WO 0109362 discloses a procedure to select variant bacteria that are more tolerant of the killing effect of the high field electrical pulse used in the electroporation procedure.

BRIEF SUMMARY OF THE INVENTION

The present invention provides a bacterium having a genome that is genetically engineered to be at least two percent (2%) to fifteen percent (15%) smaller than the genome of its native parent strain. When used to produce a product, a bacterium with a smaller genome can have one or more of the following advantages. One, the production process can be more efficient either in terms of resource consumption or in terms of production speed, or both. Two, the product purification process can be simplified or purer products can be made. Three, a product that cannot be produced before due to native protein interference can be produced. Fourthly, as described here, the reduced genome bacteria has an improved competence for transformation.

The present invention is also directed toward a method for culturing bacteria for transformation events. The method also results in improved transformation efficiencies and can be used with or without the reduced genome bacteria.

It is an advantage of the present invention that the reduced genome bacteria and the method for culturing the bacteria can be used together to maximize transformation efficiency.

Other objects, features and advantages of the invention will become apparent upon consideration of the following detailed description.

DETAILED DESCRIPTION OF THE INVENTION

In this specification, we address the transformation competence of bacterial cells in general, and in particular cells of *E. coli*. First it was found that *E. coli* strains which had the size of their genomes reduced by a series of deletions of genetic material also proved to be highly competent for transformation events. Second, in the course of working with the transformation competent *E. coli*, a methodology was developed for culturing bacterial strains to prepare them for transformation. These two insights are preferable used together, but are also useful separately. The reduced genome *E. coli* have improved transformation competence regardless of the methods used and the method can be used to render other bacterial strains more competent. However, the best transformation efficiencies will be recognized by using the reduced genome *E. coli* strains in the methodology described here. While the description of the method for reducing the genome of *E. coli* are lengthy, that aspect will be discussed here first, after which the discussion will return to transformation competence and the methodology.

The workers here developed several methods for deleting genomic DNA from a genome without leaving any inserted DNA behind. If one is making several sequential deletions from the single DNA molecule which makes up a bacterial genome, it is important not to leave any inserted DNA sequences behind. Such inserted sequences, if they were left behind, would be candidate sites for undesired recombination events that would delete uncharacterized and perhaps important portions of the remaining genome from the bacteria or cause other unanticipated genome rearrangements with untoward effects. Since one of the objectives of the genome reduction effort is to increase the genetic stability of the bacteria, leaving any inserted DNA behind would be contrary to the objective, and should be avoided. Thus the methods used to delete DNA from the genome become important and sophisticated.

In one aspect, the present invention relates to a bacterium having a genome that is genetically engineered to be smaller than the genome of its native parent strain. For exemplary purposes, the work described here has focused on the common laboratory and industrial bacterium *Escherichia coli*. The genome reduction work described here began with the laboratory *E. coli* strain K12, which had prior to the work described here, a genome of 4,639,221 nucleotides or base pairs. The bacterium of the present invention can have a genome that is as much as 14% to 16%, smaller than the genome of its native parental strain. We have so far reduced the genome of *E. coli* K12 by a little over fourteen percent (14.1%), without disabling the bacteria from its protein production utility. The term "native parental strain" means a bacteria strain found in natural or native environment as commonly understood by the scientific community and on whose genome a series of deletions can be made to generate a bacterial strain with a smaller genome. The percentage by which a genome has become smaller after a series of deletions is calculated by dividing "the total number of base pairs deleted after all of the deletions" by "the total number of base pairs in the genome before all of the deletions" and then multiplying by 100. The strain of *E. coli* with the 14% genome reduction has been named MDS39, so-named because thirty-nine deletions of material from the genome been performed from the parental strain MG1655.

Below, *E. coli* is used as an example to illustrate the genes and other DNA sequences that are candidates for deletion in order to generate a bacterium that can produce a desired product more efficiently. The general principles illustrated and the types of genes and other DNA sequences identified as candidates for deletion are applicable to other bacteria species or strains. It is understood that genes and other DNA sequences identified below as deletion candidates are only examples. Many other *E. coli* genes and other DNA sequences not identified may also be deleted without affecting cell survival and proliferation to an unacceptable level.

It is assumed in the analysis and methodology described below that the DNA sequence of the target bacterial strain is available. The full genomic sequence of several strains of *E. coli* is, of course, now published (for example, Blattner et al, Science, 277:1453-74, 1997; Pema et al, nature, 409,529-533,2001; Hayashi et al, DNA Res., 8, 11-22, 2001), as is the sequence of several other commonly used laboratory bacteria. To start the deletion process, the genome of the bacteria is analyzed to look for those sequences that represent good candidates for deletion. Of course, these techniques can also be applied to partially sequenced genomes in the genomic areas for which sequence date is available or could be determined.

In *E. coli*, and other bacteria as well, as well as in higher organisms, a type of DNA sequence that can be deleted includes those that in general will adversely affect the stability of the organism or of the gene products of that organism. Such elements that give rise to instability include transposable elements, insertion sequences, and other "selfish DNA" elements. For example, insertion sequence (IS) elements and their associated transposes are often found in bacterial genomes, and thus are targets for deletion. IS sequences are common in *E. coli*, and all of them may be deleted. For purposes of clarity in this document, we use the term IS element generically to refer to DNA elements, whether intact or defective, that can move from one point to another in the genome. An example of the detrimental effects of IS elements in science and technology is the fact that they can hop from the genome of the host *E. coli* into a BAC plasmid during propagation for sequencing. Many instances are found in the human genome and other sequences in the GenBank database. This artifact could be prevented by deletion from the host cells of all IS elements. For a specific application, other specific genes associated with instability may also be deleted.

Figure 1:
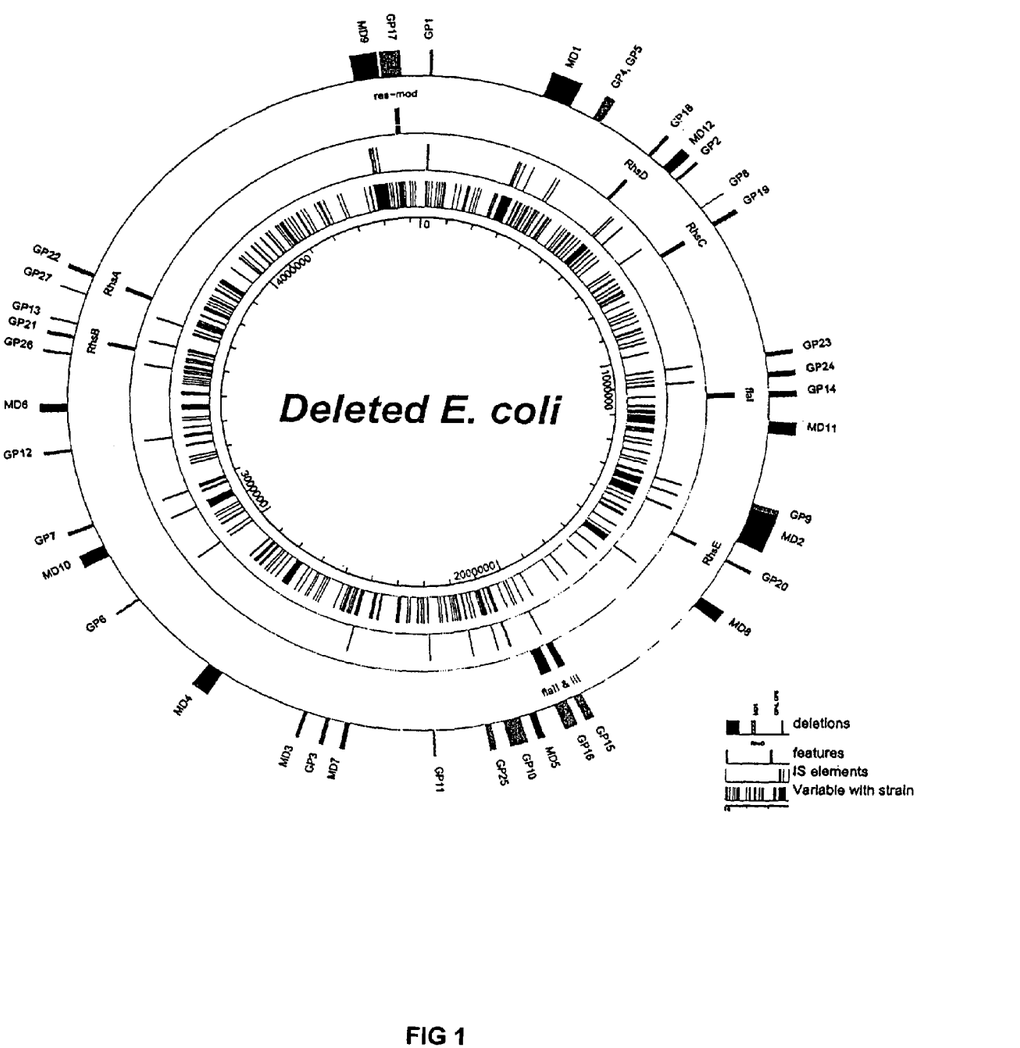
FIG. 1 shows positions of the genes and other DNA sequences on *E. coli* K-12 bacterial genome that were candidates for deletion as black and lighter hatched boxes on the outermost ring.

Shown in FIG. 1 is illustration of the *E. coli* genome, which natively, in the K12 strain, comprises 4,639,221 base pairs. FIG. 1, shows, on the inner ring, the scale of the base pair positions of the *E. coli* K12 genome (strain MG1655), scaled without deletions. The next ring progressively outward shows regions of the K12 genome that are missing or highly altered in a related strain O157:H7, and which are thus potentially deletable from the K12 genome. The next ring outward shows the positions of the IS elements, both complete and partial, in the native genome. The next ring moving outward shows the positions of the RHS elements A to E and flagellar and restriction regions specially targeted for deletion here. The outermost ring shows the location of the deletions actually made to the genome, as also listed in Tables 1 and 2 below. These deletions make up about 14 percent of the base pairs in the original K12 MG 1655 genome.

Another family of E. coli genes that can be deleted is the flagella gene family. Flagella are responsible for motility in bacteria. In natural environments, bacteria swim to search for nutrients. In cultured environments, bacteria motility is not important for cell survival and growth and the swimming action is metabolically very expensive, consuming over 1% of the cellular energy to no benefit. Thus, the flagella genes may be deleted in generating a bacterium with a smaller genome. Positions of flagella genes on an E. coli genome map are shown in FIG. 1 and Table 1.

Another family of E. coli genes that can be deleted is the restriction modification system and other nucleases whose products destroy foreign DNA. These genes are not important for bacterial survival and growth in culture environments. These genes can also interfere with genetic engineering by destroying plasmids introduced into a bacterium. Thus, these genes can be deleted in generating a bacterium with a smaller genome. Positions of restriction modification system genes on an E. coli genome map are shown in FIG. 1 and Table 1.

One type of E. coli DNA element, already mentioned, that can be deleted is the IS elements. IS elements are not important for bacteria survival and growth in a cultured environment and are known to interfere with genome stability. Thus, the IS elements can be deleted in generating a bacterium with a smaller genome. Positions of the IS elements on an E. coli genome map are shown in FIG. 1 and Table 1.

Another type of E. coli DNA element that can be deleted is the Rhs elements. All Rhs elements share a 3.7 Kb Rhs core, which is a large homologous repeated region (there are 5 copies in E. coli K-12) that provides a means for genome rearrangement via homologous recombination. The Rhs elements are accessory elements which largely evolved in some other background and spread to E. coli by horizontal exchange after divergence of E. coli as a species. Positions of the Rhs elements on an E. coli genome map are shown in FIG. 1 and Table 1.

One type of region in the E. coli genome that can be deleted is the non-transcribed regions because they are less likely to be important for cell survival and proliferation. Another type of regions in the E. coli genome that can be deleted is the hsd regions. The hsd regions encode for the major restriction modification gene family which has been discussed above. Positions of the non-transcribed regions and the hsd regions on an E. coli genome map are shown in FIG. 1 and Table 1.

One general method to identify additional genes and DNA sequences as deletion candidates is to compare the genome of one bacterial strain to another. Any DNA sequences that are not present in both strains are less likely to be functionally essential and thus can be used for identifying candidates for deletion. In the examples described below, the complete genomic sequences of two E. coli strains, O157:H7 EDL933 and K-12 MG1655, were compared. DNA sequences that were not found in both strains were used to identify targets for deletion. Twelve such identified targets from E. coli strain MG1655 were deleted, resulting in a bacteria strain with a genome that is about 8% smaller. The bacteria with the reduced genome are alive and grow at substantially the same rate as the native parent MG1655 strain.

One can test the consequence of deleting one or several genes or other DNA sequences from the genome. For example, after one or several genes or other DNA sequences of the genome have been deleted, one can measure the survival and proliferation rate of the resultant bacteria. Although most of the above-identified genes or other DNA sequences may be deleted without detrimental effect for purpose of producing a desired product, it is possible that the deletion of a specific gene or other DNA sequence may have an unacceptable consequence such as cell death or unacceptable level of reduction in proliferation rate. This possibility exists because of redundancies in gene functions and interactions between biological pathways. Some deletions that are viable in a strain without additional deletions will be deleterious only in combination with other deletions. The possibility exists also because of certain methods used to identify deletion candidates. For example, one method used to identify deletion candidates is to compare two E. coli strains and select genes or other DNA sequences that are not present in both strains. While the majority of these genes and other DNA sequences are not likely to be functionally essential, some of them may be important for a unique strain. Another method used to identify deletion candidates is to identify non-transcribed regions and the possibility exists that certain non-transcribed regions may be important for genome stability.

The consequence of deleting one or several genes or other DNA sequences to be tested depends on the purpose of an application. For example, when high production efficiency is the main concern, which is true for many applications, the effect of deletions on proliferation rate and medium consumption rate can be the consequence tested. In this case, the consequence tested can also be more specific as the production speed and quantity of a particular product. When eliminating native protein contamination is the main concern, fewer native proteins and lower native protein levels, or the absence of a specific native protein, can be the consequence tested.

Testing the consequence of deleting a gene or other DNA sequence is important when little is known about the gene or the DNA sequence. Though laborious, this is another viable method to identify deletion candidates in making a bacterium with a reduced genome. This method is particularly useful when candidates identified by other methods have been deleted and additional candidates are being sought.

When the consequence of deleting a gene or other DNA sequence has an effect on the viability of the bacteria under a set of conditions, one alternative to not deleting the specific gene or other DNA sequence is to determine if there are measures that can mitigate the detrimental effects. For example, if deleting lipopolysaccharide (LPS) genes results in poor survival due to more porous cellular membranes caused by the absence from the cellular membranes of the transmembrane domain of the LPS proteins, culture conditions can be changed to accommodate the more porous cellular membranes so that the bacteria lacking the LPS genes can survive just as well as the bacteria carrying the LPS genes.

Methods for deleting DNA sequences from bacterial genomes that are known to one of ordinary skill in the art can be used to generate a bacterium with a reduced genome.

Examples of these methods include but are not limited to those described in Posfai, G. et al., *J. Bacteriol.* 179: 4426-4428 (1997), Muyrers, J. P. P. et al., *Nucl. Acids Res.* 27:1555-1557 (1999), Datsenko, K. A. et al., *Proc. Natl. Acad. Sci.* 97:6640-6649 (2000) and Posfai, G. et al., *Nucl. Acids Res.* 27: 4409-4415 (1999), all of which are hereby incorporated by reference in their entirety. Basically, the deletion methods can be classified to those that are based on linear DNAs and those that are based on suicide plasmids. The methods disclosed in Muyrers, J. P. P. et al., *Nucl. Acids Res.* 27:1555-1557 (1999) and Datsenko, K. A. et al., *Proc. Natl. Acad. Sci.* 97:6640-6649 (2000) are linear DNA-based methods and the methods disclosed in Posfai, G. et al., *J. Bacteriol.* 179: 4426-4428 (1997) and Posfai, G. et al., *Nucl. Acids Res.* 27: 4409-4415 (1999) are suicide plasmid-based methods.

Some known methods for deleting DNA sequences from bacterial genomes introduce extraneous DNA sequences into the genome during the deletion process and thus create a potential problem of undesired homologous recombination if any of the methods is used more than once in a bacterium. To avoid this problem, scarless deletion methods are preferred. By scarless deletion, we mean a DNA sequence is precisely deleted from the genome without generating any other mutations at the deletion sites and without leaving any inserted DNA in the genome of the organism. However, due to mistakes, such as those made in PCR amplification and DNA repairing processes, one or two nucleotide changes may be introduced occasionally in scarless deletions. Described below are some novel scarless deletion methods, either linear DNA-based or suicide plasmid-based. These novel methods have been applied to *E. coli* strains in the examples described below. It is understood that the specific vectors and conditions used for *E. coli* strains in the examples can be adapted by one of ordinary skill in the art for use in other bacteria. Similar methods and plasmids can be used to similar effect in higher organisms. In some instances it may be more appropriate to modify an existing production strain rather than transfer production to the minimized genome *E. coli* strain.

Novel Linear DNA-Based Scarless Deletion Method I

Figure 2:
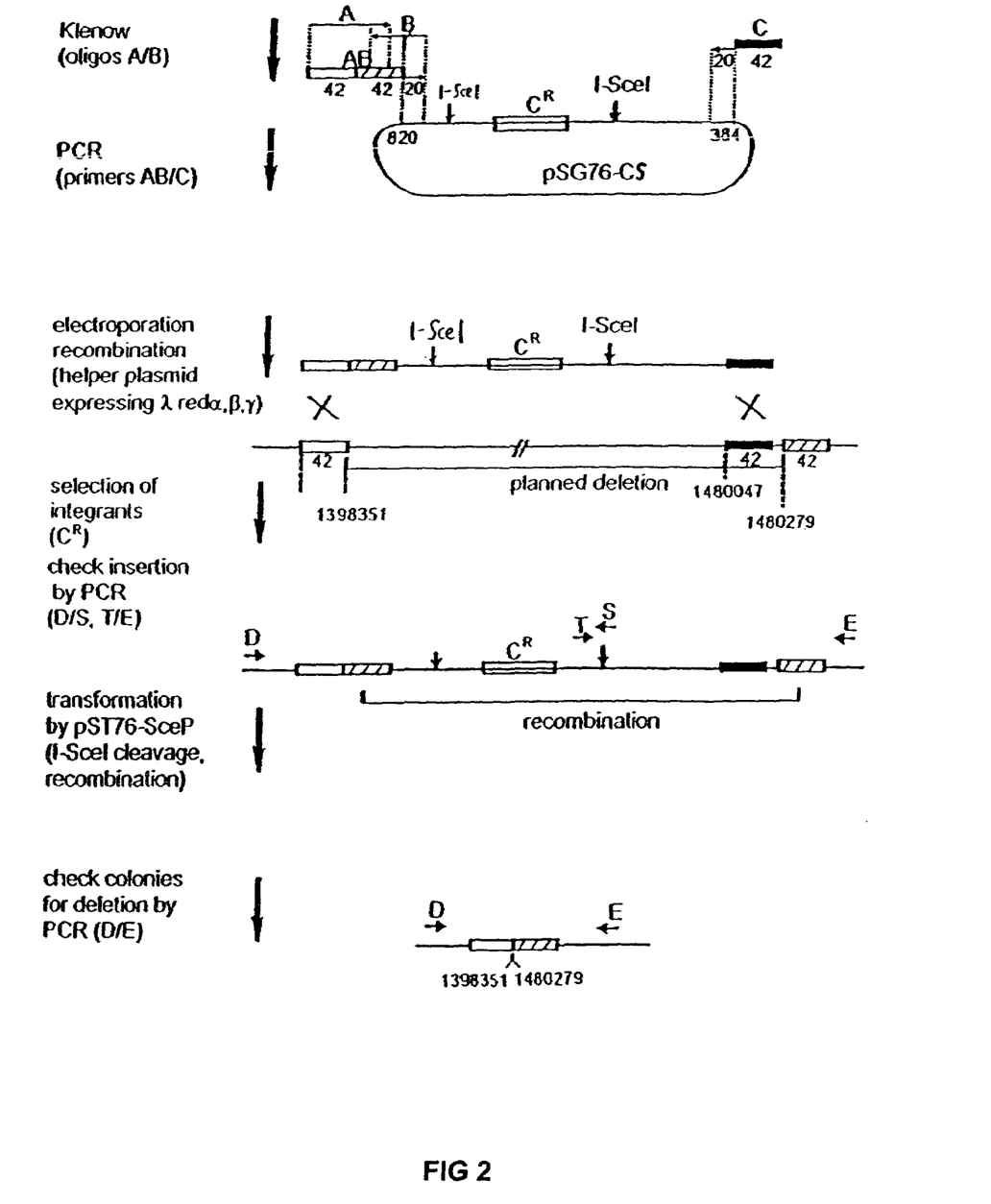
FIG. 2 illustrates a specific example of a linear DNA-based scarless genetic modification method of the present invention.
Figure 3:
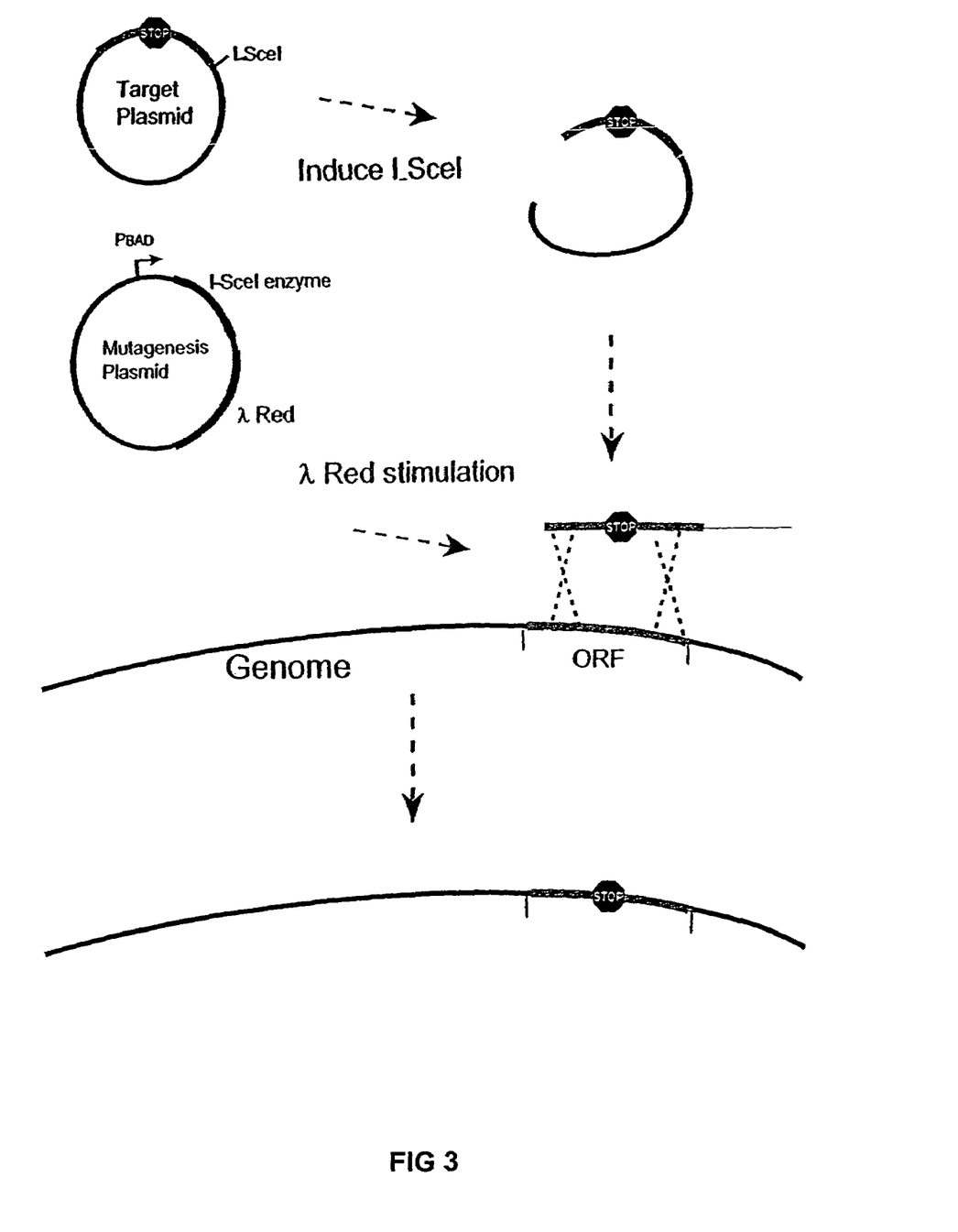
FIG. 3 illustrates a specific example of another linear DNA-based method of the present invention.
Figure 4:
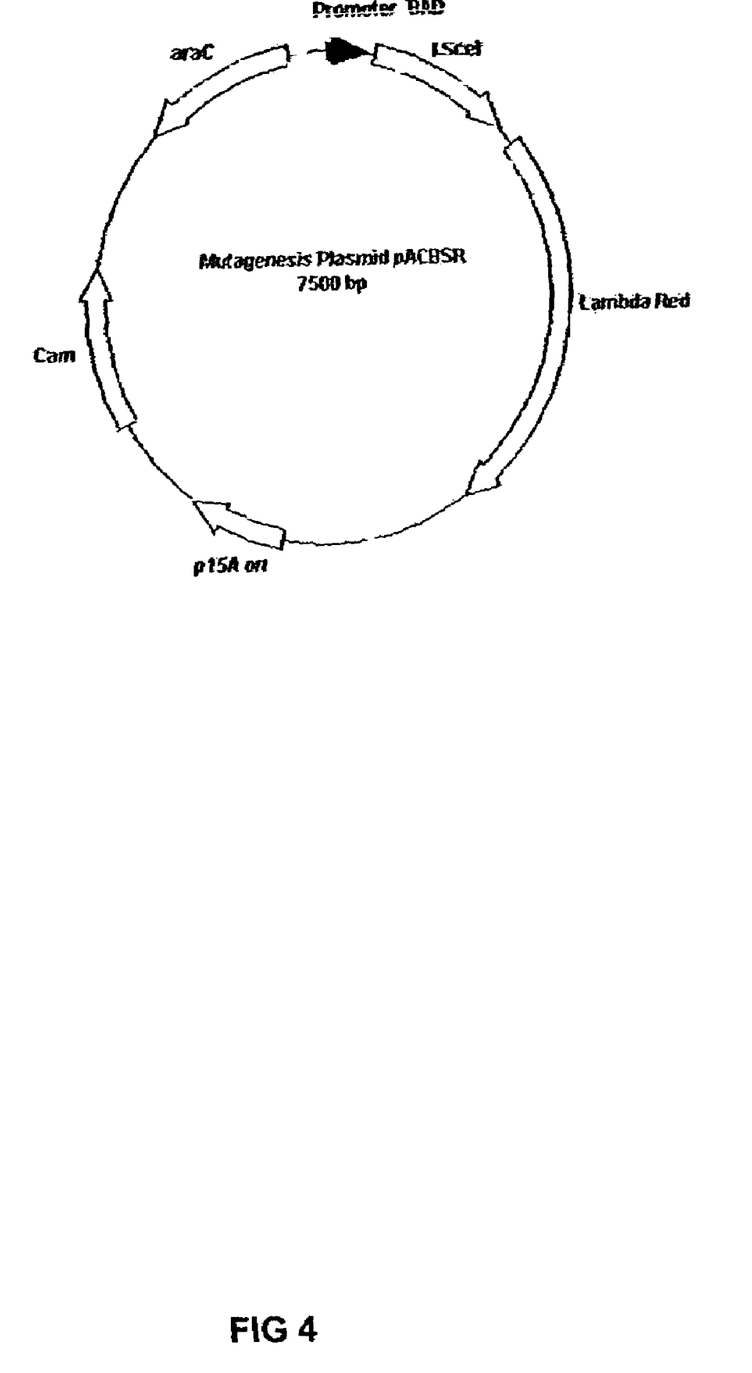
FIG. 4 shows a mutagenesis plasmid that can be used in the linear DNA-based method illustrated in FIG. 3.

The novel DNA-based scarless deletion method of the present invention can be best understood when the following description is read in view of FIG. 2. Generally speaking, the method involves replacing a segment of the genome, marked for deletion, with an artificial DNA sequence. The artificial sequence contains one or more recognition sites for a sequence-specific nuclease such as I-SceI, which cuts at a sequence that does not occur natively anywhere in the *E. coli* K12 genome. Precise insertion of the linear DNA molecule into the genome is achieved by homologous recombination aided by a system that can increase the frequency of homologous recombination. When the sequence-specific nuclease is introduced into the bacteria, it cleaves the genomic DNA at the unique recognition site or sites, and only those bacteria in which a homologous recombination event has occurred will survive.

Referring specifically to FIG. 2, the plasmid pSG76-CS is used as a template to synthesize the artificial DNA insert. The artificial insertion sequence extends between the sequences designated A, B and C in FIG. 2. The $C^R$ indicates a gene for antibiotic resistance. The insert DNA is PCR amplified from the plasmid and electroporated into the *E. coli* host. The insert was constructed so that the sequences A and B match sequences in the genome of the host which straddle the proposed deletion. Sequence C of the insert matches a sequence in the host genome just inside sequence B of the host genome. Then the bacteria are selected for antibiotic resistance, a selection which will be survived only by those bacteria in which a homologous recombination event occurred in which the artificial DNA inserted into the bacterial genome. This recombination event occurs between the pairs of sequences A and C. The inserted DNA sequence also includes a sequence B, now positioned at one end of the insert, which is designed to be homologous to a sequence in the genome just outside the other end of the insert, as indicated in FIG. 2. Then, after growth of the bacteria, the bacteria is transformed with a plasmid, pSTKST, which expresses the I-SceI sequence-specific nuclease. The I-SceI enzyme cuts the genome of the bacteria, and only those individuals in which a recombination event occurs will survive. 10-100% of the survivors are B to B recombination survivors, which can be identified by a screening step. The B to B recombination event deletes the entire inserted DNA from the genome, leaving nothing behind but the native sequence surrounding the deletion.

To repeat, the first step of the method involves providing a linear DNA molecule in a bacterium. The linear DNA molecule contains an artificial linear DNA sequence that has the following features: one end of the linear DNA sequence is a sequence identical to a genome sequence on the left flank of the genome region to be deleted, followed by a sequence identical to a genome sequence on the right flank of the genome region to be deleted; the other end of the linear DNA molecule is a sequence identical to a genome sequence within the genome region to be deleted; between the two ends of the linear DNA, there is a recognition site that is not present in the genome of the bacterial strain and an antibiotic selection gene. The artificial DNA sequence can be made using polymerase chain reaction (PCR) or directed DNA synthesis. A PCR template for this purpose contains the unique recognition site and the genomic DNA sequences on both ends of the artificial linear DNA sequence are part of the primers used in the PCR reaction. The PCR template can be provided by a plasmid. An example of a plasmid that can be used as a template is pSG76-C (GenBank Accession No. Y09893), which is described in Posfai, G. et al., *J. Bacteriol* 179: 4426-4428 (1997). pSG76-CS (GenBank Accession No. AF402780), which is derived from pSG76-C, may also be used. pSG76-CS contains the chloramphenicol resistance ($Cm^R$) gene and two I-SceI sites, and was obtained by the PCR-mediated insertion of a second I-SceI recognition site into pSG76-C, downstream of the NotI site. The two I-SceI sites are in opposite direction.

An artificial or constructed DNA sequence can be provided to a bacterium by directly introducing the linear DNA molecule into the bacterium using any method known to one of ordinary skill in the art such as electroporation. In this case, a selection marker such as an antibiotic resistance gene is engineered into the artificial DNA sequence for purpose of selecting colonies containing the inserted DNA sequence later. Alternatively, a linear DNA molecule can be provided in a bacterium by transforming the bacterium with a vector carrying the artificial linear DNA sequence and generating a linear DNA molecule inside the bacterium through restriction enzyme cleavage. The restriction enzyme used should only cut on the vector but not the bacterial genome. In this case, the artificial linear DNA sequence does not have to carry a selection marker because of the higher transformation efficiency of a vector so that a bacterium with the inserted linear DNA can be screened by PCR later directly.

The second step of the scarless deletion method involves replacement of a genomic region by insertion of the artificial DNA molecule. The bacterial cells are engineered to contain a system that increases the frequency of homologous recombination. An example of such a system is the Red recombinase system. The system can be introduced into bacterial cells by a vector. The system helps the linear DNA molecule to replace a genomic region which contains the deletion target. As described in the examples below, a vector carrying a homologous recombination system that can be used in *E. coli* is pBADαβγ, which is described in Muyrers, J. P. P. et al., *Nucl. Acids Res.* 27:1555-1557 (1999). Another plasmid pKD46 described in Datsenko, K. A. et al., *Proc. Natl. Acad. Sci.* 97:6640-6649 (2000) may also be used. Other plasmids that can be used include pGPXX and pJGXX. pGPXX is derived from pBADαβγ by replacing the origin of replication in pBADαβγ with pSC101 origin of replication. pJGXX is a pSC101 plasmid that encodes the Red functions from phage 933W under tet promoter control The third step of the scarless deletion method involves removal of the inserted DNA sequence. An expression vector for a sequence-specific nuclease such as I-SceI that recognizes the unique recognition site on the inserted DNA sequence is introduced into the bacteria. The sequence-specific nuclease is then expressed and the bacterial genome is cleaved. After the cleavage, only those cells in which homologous recombination occurs resulting in a deletion of the inserted linear DNA molecule can survive. Thus, bacteria with a target DNA sequence deleted from the genome are obtained. Examples of sequence-specific nuclease expression vectors that can be used in *E. coli* include pKSUC1, pKSUC5, pSTKST, pSTAST, pKTSHa, pKTSHc, pBAD-Sce1 and pBADSce2. The sequence-specific nuclease carried by these vectors is I-SceI. pKSUC1, pKSUC5, pSTKST and pSTAST are described below in the examples.

The method described above can be used repeatedly in a bacterium to generate a series of deletions. When the expression vector for the homologous recombination system and the expression vector for the unique sequence-specific nuclease are not compatible with each other, such as the case for pBADαβγ and pKSUC1, transformation of the two vectors have to be performed for each deletion cycle. Transformation of the two vectors can be avoided in additional deletion cycles when two compatible plasmids, such as pBADαβγ and pSTKST, or pKD46 and pKSUC5, are used. An example of using two of these vectors that are compatible with each other is described in the examples below.

The above scarless deletion method can be modified to make a series of deletions on a bacterial genome more efficient. The first step of the modified method involves making insertions of a linear DNA molecule individually in bacterial cells, preferably wild-type bacteria cells, in a parallel fashion, resulting in a set of strains, each carrying a single insertion. This step can be carried out as described above. The second step of the modified method involves sequentially transferring individual insertions into the target cell whose genome is to be reduced. P1 transduction is an example of the methods that can be used for transferring insertions. The third step of the modified method involves recombinational removal of the inserted sequence, which can be carried out as described above.

Other DNA-Based Scarless Deletion Methods

There are other alternative methods for deletion of genomic DNA from a bacterial strains. In the interests of brevity, they will not be discussed further here, except to acknowledge that they exist.

Reduced Genome *E. coli* Competence

As already mentioned above, the strain MDS39 carries a genome which is reduced in excess of 14% from that of its parental strain. This strain exhibited a high efficiency of transformation, equal to one of the best strains that is in common commercial use as an electroporation competent strain, even when grown at 37° C. and without addition of sorbitol or other sugars. This high efficiency of transformation extended to BAC DNA of a large size that generally transforms with a much lower efficiency than small DNA. This makes the strain MDS39 particularly valuable as a vehicle for cloning DNA for the wide range of applications noted above, since not only is it potentially safer and cleaner because of the deletion of many unnecessary genes that might cause contamination, but it also exhibits an unusually high efficiency of transformation by electroporation. The beneficial characteristics of MDS39 were also present in an earlier strain in the genome deletion series, MDS31.

Further experimentation have also shown that strain MDS41-R13 (41 deletions), the first multi-deletion strain to be completely clear of all Insertion Sequences (ISs) also is capable of high efficiency transformation with both small plasmid (pBR322 and large DNA (100 kb BAC). This shows that this beneficial characteristic is heritable in strains derived from MDS39, and indeed from MDS31 and even earlier strains in the deletion sequence, by additional genetic modification. It is not known if the trait of competence is created by the deletion of one or more of the genetic elements from the bacterial genome, or if it is a cumulative by-product of the many transformation events performed on the strains as the strains were made.

While both *E. coli* MG1655 and MDS41-R13 grow well in LB medium, the stationary phase cell density is limited and the medium becomes quite alkaline, probably sufficiently alkaline to curtail growth. Furthermore, while strain MDS41-R13 grows as fast as MG1655 in the exponential growth phase, it exhibits a lag phase which is not exhibited by MG1655. Competent cells prepared from *E. coli* MDS41-R13 grown in LB show higher transformation efficiency than MG1655 grown under the same conditions. The transformation efficiency of MDS41-R13 is surprisingly high, given that the cells can be grown out at 37° C. and no sorbitol or other sugars have been added. Data presented below shows that MDS41-R13 and MDS40 grow at about the same rate (as measured by the doubling times) in exponential phase as MG1655. In baffled flasks, the growth rates are higher (doubling time lower) than in the unbaffled flasks. Both MDS41-R13 and MDS40 exhibit the lag phase seen in the examples below, but not seen in MG1655. The longer the seed cultures are incubated, the longer is the lag phase.

Methodology

In trying to improve the sub-optimal growth particularly of the MDS strains, we first tried adding glucose to the medium to provide a better carbon source, however, the medium became very acidic, and growth of MG1655 halted at a lower stationary phase cell density than in LB without glucose (OD650=1.0 compared with 2.0 for LB). Adding phosphate to act as a pH buffer improved the growth, presumably by absorbing the hydrogen ions produced during growth on glucose. So-called Terrific Broth, which was originally developed for plasmid DNA production (Tartoff and Hobbs) has the composition, per liter of medium, Tryptone 12 g, Yeast Extract 24 g, potassium dihydrogen phosphate 9.4 g, di-potassium hydrogen phosphate 2 g, and glycerol as the carbon source. Glycerol is known to produce less acid in fermentations when it is used as the main carbon source. We discovered that *E. coli* strains MDS41-R13 and MG1655 grew extremely well in Terrific Broth (TB). While the doubling time, 36 minutes was very slightly slower in TB compared with LB, in Terrific Broth, MDS41-R13 reached 5-6 times the cell density of an LB culture, and MG1655 reached approximately 3 times the cell density. Furthermore, MDS41-R13 did not exhibit any lag phase in Terrific Broth.

*E. coli* strain MDS41-R13 was found to transform by electroporation with high efficiency when grown in TB. We first tried harvesting the cells at OD650=0.5, as recommended for LB, and found that the transformation efficiency when used in electroporation was surprisingly high compared with cells grown in the conventionally used LB medium. We then tried harvesting at OD650=1.0, and surprisingly, the transformation efficiency was still high. Even more surprisingly, when the cells were harvested at OD650=2 to 2.2, the cells were still highly efficient, as seen in the examples below. The literature teaches that electrocompetence falls off rapidly if cells are allowed to grow to an OD greater than 0.5 to 0.6. The efficiency of some of the cells prepared from cultures grown in TB to an OD650 of around 2 has exceeded $10^{10}$ transformants per microgram of pUC19. This is an unexpectedly high level of transformation, not only because of the high cell density at harvest, but also in view of the fact that the cultures were grown at 37° C., which the literature teaches leads to lower transformation efficiency than growth at 18-26° C.

It is believed that the superiority of the Terrific Broth treatment is due to the use of glycerol as the main carbon source. By using glycerol as the carbon source, the cultures produce less acid and therefore grow longer under limited oxygen concentrations, as compared with what would be the case with other carbon sources. Good nutrient concentrations and good pH buffering may also play a part. It is also an advantage of this medium that the cultures may be maintained at higher temperatures, over 28° C., and as high as about 37° C. This temperature permits continued grow of the culture. While the results here were obtained with baffled flasks, the same results can be expected in commercial fermentors and other culture vessels.

The above disclosure generally describes the present invention. The invention will be more fully understood upon consideration of the following examples which are provided herein for purposes of illustration only and are not intended to limit the scope of the invention.

EXAMPLES

Plasmids

The plasmid used for PCR construction of the artificial inserted DNA sequence was designated pSG76-CS (GenBank Accession No. AF402780), which was derived from pSG76-C (Posfai, G. et al., *J. Bacteriol.* 179: 4426-4428 (1997)) by inserting a second I-SceI site. The second I-SceI site was obtained by the PCR-mediated insertion of a second I-SceI recognition site into pSG76-C, downstream of the NotI site. The two I-SceI sites are in opposite direction.

The pBADαβγ plasmid was used for enhancing recombination of linear DNA-fragments into the genome. This plasmid was described in Muyrers, J. P. P. et al., *Nucl. Acids Res.* 27:1555-1557 (1999).

The PKSUC1 plasmid (GenBank Accession No. AF402779), for expressing I-SceI, was derived from pSG76-K (Posfai, G. et al., *J. Bacteriol.* 179: 4426-4428 (1997)) and pUC19RP12 (Posfai, G. et al., *Nucl. Acids Res.* 27: 4409-4415 (1999)). The XbaI-NotI fragment (carries the Kan gene; the NotI end was blunted by Klenow polymerase) of pSG76-K was ligated to the XbaI-DraI fragment (carries the I-SceI gene and the pUC ori) of pUC19RP12.

The pKSUC5 plasmid for tetracycline-regulated expression of I-SceI was derived from pFT-K (Posfai, G. et al., *J. Bacteriol.* 179: 4426-4428 (1997)) and pKSUC1. The large XbaI-NcoI fragment of pKSUC1 was ligated to the XbaI-NcoI fragment of pFT-K carrying the tet repressor.

The PKD46 plasmid for enhancing recombination of linear DNA-fragments into the genome was described in Datsenko, K. A. et al., *Proc. Natl. Acad. Sci.* 97:6640-6649 (2000).

The plasmid pSTKST (GenBank Accession No. AF406953) is a low copy number $Kan^R$ plasmid for chlortetracycline-regulated expression of I-SceI, derived from pFT-K (Posfai, G. et al., *J. Bacteriol.* 179: 4426-4428 (1997)) and pUC19RP12 (Posfai, G. et al., *Nucl. Acids Res.* 27: 4409-4415 (1999)). The XbaI-PstI fragment from pUC19RP12, carrying the I-SceI gene, was ligated to the large XbaI-PstI fragment of pFT-K. This plasmid expresses I-SceI when induced by chlortetracycline. Replication of the plasmid is temperature-sensitive (Posfai, G. et al., *J. Bacteriol.* 179: 4426-4428 (1997)).

The plasmid pSTAST, a low copy number $Ap^R$ plasmid for chlortetracycline-regulated expression of I-SceI, was derived from pFT-A (Posfai, G. et al., *J. Bacteriol.* 179: 4426-4428 (1997)) and pUC19RP12 (Posfai, G. et al., *Nucl. Acids Res.* 27: 4409-4415 (1999)). The XbaI-PstI fragment from pUC19RP12, carrying the I-SceI gene, was ligated to the large XbaI-PstI fragment of pFT-A. This plasmid expresses I-SceI when induced by chlortetracycline. Replication of the plasmid is temperature-sensitive (Posfai, G. et al., *J. Bacteriol.* 179: 4426-4428 (1997)).

Procedure 1

This describes the process used to repeatedly make deletions from the genome of *E. coli* K12. This procedure is a scarless deletion method. The procedure begins with the construction of a linear target fragment by PCR. This was done by mixing 20 pmol of primer A with 20 pmol primer B, and performing PCR in a total volume of 50 µl. The cycle parameters used were 15×(94° C. 40 sec/57° C. or lower (depending on the overlap of A and B) 40 sec/72° C. 15 sec). The 1 µl of the PCR mix above were taken, added to 20 pmol of primers A and C each, add 50 ng of pSG76-CS and perform PCR in a volume of 2×50 µl (use 50-µl tubes, and two tubes are combined to have more DNA). The cycle parameters used were 28×(94° C. 40 sec/57° C. 40 sec/72° C. 80 sec). To purify the PCR mix from the above step, Promega Wizard PCR purification kit was used. The resulting DNA fragment was suspended in 20 µl water.

Next was the replacement of a genomic region by insertion of the artificial DNA-fragment. This was done by taking the target cell carrying pBADαβγ and preparing electrocompetent cells as described (Posfai, G. et al., *Nucl. Acids Res.* 27: 4409-4415 (1999)), except that 0.1% arabinose was added to the culture 0.25-1 hour before harvesting the cells. 4 µl of DNA fragments (100-200 ng) were electroporated into 40 µl of electrocompetent cells. The cells were plated on Cam plates (25 µg cam/ml) and incubated at 37° C. The usual result was to obtain a total of 10 to several hundred colonies after overnight incubation. A few colonies were checked for correct site insertion of the fragment by PCR using primers D and E.

Next was the deletion of the inserted sequences. This was done by preparing competent cells derived from a selected colony from above by the $CaCl_2$ method (Sambrook, J. et al., Molecular Cloning: A Laboratory Manual. Cold Spring Harbor Laboratory Press, Cold Spring Harbor, N.Y. (1989)). The plasmid pKSUC1 (~100 ng) was transformed into the cells by standard procedures (Sambrook, J. et al., Molecular Cloning: A Laboratory Manual. Cold Spring Harbor Laboratory Press, Cold Spring Harbor, N.Y. (1989)). The cells were plated on Kan plates and incubated at 37° C. (pKSUC1 and pBADαβγ are incompatible, thus selection on Kan eliminates pBADαβγ from the cells). The colonies were checked for correct deletion by PCR using primers D and E. A colony was selected carrying the correct deletion. At this point, the cells carried pKSUC1. The next step is to delete this plasmid.

This deletion is done through the replacement of pKSUC 1 with pBADαβγ. A colony from the prior step was selected, grown in LB at 37° C. under nonselective conditions, reinoculating the cells into fresh medium 2-3 times. Competent cells were prepared for either chemical transformation or electroporation. The plasmid pBADαβγ (100-200 ng) was transformed into the competent cells which were plated on Amp plates. A colony which was Kan sensitive/Amp resistant was selected by toothpicking a hundred colonies on Kan and Amp plates.

The selected colony can be used in a next round of deletion by using a new targeting fragment and repeating the steps above. If no more deletions are needed, growing the cells under nonselective conditions (no Amp is added) results in the spontaneous loss of pBADαβγ from a large fraction of the cells.

Procedure 2

This procedure is similar to procedure 1, but pKSUC1 is replaced by pSTKST. This plasmid is compatible with pBADαβγ, has a temperature-sensitive replicon, and expression of I-SceI requires induction by chlortetracyclin (CTC). The advantage is that elimination of pSTKST from the cell is easily accomplished by growing the culture at 42° C.

Construction of a linear targeting fragment by PCR and replacement of a genomic region by insertion of the fragment are done as described in Procedure 1.

To delete the inserted sequences competent cells are prepared from a culture derived from a selected colony harboring the right insertion. Cells are transformed by pSTKST, plated on Kan+Cam plates and incubated at 30° C. A colony from this plate is inoculated into 10 ml of LB+Kan supplemented with heat-treated inducer cTc (25 µg/ml final concentration) and grown at 30° C. for 24 hours. This step serves induction of the expression of I-SceI. Dilutions of the culture are then spread on LB+Kan plates and incubated overnight at 30° C. 6-12 colonies were checked for correct deletion by PCR using primers D and E. A colony was selected carrying the correct deletion.

To eliminate the helper plasmids from the cell, the culture is grown at 42° C. in LB (no antibiotics added).

Procedure 3

Since pBADαβγ and pSTKST carry compatible replicons, repeated transformations of the plasmids are not required when consecutive deletions are made in the same host. The two plasmids are maintained in the host cell throughout consecutive deletion constructions by antibiotic selection (Kan+Amp). Recombinase and specific nuclease functions are induced only when needed. Since replication of pSTKST is temperature-sensitive, cells must be grown at 30° C.

The procedure is identical to Procedure 2, except that pBADαβγ and pSTKST are transformed into the cell only once, and until maintenance of both plasmids in the cell is desired, the culture is grown at 30° C., and Amp+Kan are included in the medium. Note: Sometimes we experienced difficulties in growing the cells at 30° C. in the presence of two (Amp+Kan) or three (Amp+Kan+Cam) antibiotics.

Procedure 4

This is the preferred procedure when several consecutive deletions are to be made in the same cell. Insertions (recombination of linear fragments into the genome of a host cell carrying pBADαβγ) are made in parallel, creating a series of recombinant cells, each carrying a single insertion. These insertions are then transferred one by one by P1 transduction into the cell carrying pSTKST and harboring all previous deletions. Removal of all foreign sequences is done in this final host by inducing pSTKST. Compared to the previous methods, the main difference is that the insertion step and removal of the inserted sequences are done in separate cells. Since insertions are made in parallel, the construction of consecutive deletions is faster. Another advantage is that cells are transformed by the plasmids only at the beginning of the first deletion construction.

Technically the procedure is identical to Procedure 2, except that individual insertions are transferred by P1 transduction to the deletion strain already harboring pSTKST. After each P1 transduction step, I-SceI expression is induced to remove the inserted sequences.

Results

Forty-one consecutive genomic deletions have been made from *E. coli* strain K12 MG1655. The twelve deleted regions were selected for deletion, in part, as a result of comparison of the genomic DNA sequences of *E. coli* strain O157:H7 EDL933 and strain K-12 MG1655. The deletions are listed on Table 1 below. The sequence numbering is taken from the published K12 sequence.

The first deletion MD1 was made using the method described in Posfai, G. et al., *Nucl. Acids Res.* 27: 4409-4415 (1999). Using this method for creating MD1 deletion left a 114-bp pSG76-CS vector sequence, including a FRT site, in the chromosome at the site of deletion. MD2 through MD6 deletions were made using Procedure 1 described above. Deletions MD7 through MD12 were created using a combination of Procedure 4 and Procedure 1 or 2. Strain designations and genomic coordinates of each new deletion were: MD1 263080-324632; MD2 1398351-1480278; MD3 2556711-2563500; MD4 2754180-278970; MD5 2064327-2078613; MD6 3451565-3467490; MD7 2464565-2474198; MD8 1625542-1650865; MD9 4494243-4547279; MD10 3108697-3134392; MD11 1196360-1222299; MD12 564278-585331.

A total of 378,180 base pairs, which is approximately 8.1% of the native K12 MG1655 *E. coli* genome, was removed at this stage. Removing these regions from the genome did not affect bacterial survival or bacterial growth.

Table 2 below lists other segments, genes and regions of the *E. Coli* genome that were identified as candidates for further deletions. The segments have also been successfully removed from the genome of the bacteria. Again, these deletions were made without any apparent deleterious effect on the usefulness of the bacteria for laboratory and industrial use. Again the sequence designations are taken from the published K12 sequence. The two sets of deletions totaled about 14% of the original bacterial genome. Further deletions are, of course, possible.

Transformation Competence.

Making Electrocompetent Cells

Electrocompetent cells were prepared as follows. Cells were streaked out from a glycerol stock onto an LB plate, grown overnight at 37° C. Next day (sometimes colonies from older plates were used) a single colony was inoculated into 10 ml LB in a 50-ml flask, incubated at 200-220 rpm in a shaker at 37° C. overnight. From this dense starter culture, 800 μl was inoculated into 100 ml LB in a 500 ml Erlenmeyer flask, incubated in an orbital shaker at 37° C. at 200-220 rpm.

At OD=0.4 the flask was placed on ice for 20 min. From this point all manipulations were made at 0° C., tubes and solutions were chilled before use.

1. Cells were centrifuged in 2×50 ml sterile tubes at 4000 rpm/10 min.
2. Cells were suspended in 2×50 ml sterile water.
3. Cells were centrifuged at 4000 rpm/10 min.
4. Cells were suspended in 2×50 ml sterile water.
5. Cells were centrifuged at 4000 rpm/10 min.
6. Cells were suspended in 2×2 ml 10% glycerol.
7. Cells were centrifuged at 4000 rpm/10 min.
8. Cells were suspended in 2×100 μl 10% glycerol.
9. The two tubes were combined, and cells were distributed into 40 μl aliquots in Eppendorf tubes (>5 tubes), frozen on dry ice and stored at −80° C. until use. Total cell count/tube was between $10^9$ and $10^{10}$.

Electrocompetent cells were melted by keeping the tube in the hand, then placed on ice. DNA and 0.1 cm cuvettes were also kept on ice. 2 μl DNA (normally diluted to 10 ng/μl in TE) was added to the cells, mixed briefly, then pipetted in the cuvette. The cuvette was placed in an Invitrogen II device (settings: 1800 V, 50 μF, 150 Ω), and an electric pulse was applied. Cells were washed out from the cuvettes by pipetting 1 ml LB (for simplicity we used LB as recovery medium, in earlier experiments we used SOC medium) up and down in the cuvette. The mixture was transferred into a test tube and placed in a shaker for 1 h at 37° C. Appropriate dilutions were then spread on LB+antibiotics plates.

Plasmid DNAs (both small and large) were prepared according to the Promega Wizard medium prep protocol. (Growth in LB+antibiotics o/n, standard alkali lysis protocol, Promega Wizard Midicolumns, DNA recovered in TE buffer). Plasmids pBR322, pUC19 and pBeloBAC (100-kb insert) were prepared from DH5α cells. The results of the transformation events is summarized as follows.

|  | DH10B | MDS31 | MDS39 |
|---|---|---|---|
|  | Transformants per microgram | | |
| PBR322 | $2 \times 10^8$ | $2.2 \times 10^8$ | $2.7 \times 10^8$ |
| Methylated BAC | $2 \times 10^6$ | $0.6 \times 10^6$ | $1.2 \times 10^6$ |
| Unmethylated BAC | $1.8 \times 10^6$ | $4 \times 10^{3*}$ | $3 \times 10^6$ |

Electroporation of MDS41-R13 and MG1655 and DH10B

Methods were as described in the previous paragraph. The DNA was pBR322 or a 100 kb BAC DNA.

|  | Electroporation efficiency, relative to MG1655 | | |
|---|---|---|---|
|  | MDS41-R13 | MG1655 | DH10b |
| pBR322 | 0.98 | 1.00 | 0.73 |
| 100 kb BAC | 4.1* | 1.00 | 0.99 |

Absolute value 2×10⁵ transformants/microgram
Electroporation of MDS41-R13, MG1655 and DH10B.

Methods were as described above. The DNA was pBR322 DNA and pBeloBAC DNA

|  | Electroporation efficiency transformants/microgram | | |
|---|---|---|---|
|  | MDS41-R13 | MG1655 | DH10b |
| pBR322 | $3.34 \times 10^9$ | $2.4 \times 10^9$ | $3.3 \times 10^9$ |
| PBeloBAC | $1.9 \times 10^5$ | — | — |

Growth of E. coli MDS41-R13 and MG1655 in LB medium.

50 ml of sterile LB medium in two sterile 250 ml non-baffled Erlenmeyer flasks with polypropylene caps were each inoculated with a loopful of frozen glycerol stocks of MG1655 and MDS41-R13 respectively. They were grown overnight at 37° C. in an orbital shaker at 250 rpm (seed cultures). The OD650 of each culture was determined, after dilution, if needed, to stay within the linear part of the spectrophotometer range, using a microplate spectrophotometer. pH was determined using a standardized and calibrated pH meter and combination electrode. Fresh 50 ml cultures were inoculated with 500 microliters of the overnight cultures and grown in the same way as the overnight cultures. At intervals, samples were removed from the cultures and the OD650 and pH were measured as described above. The doubling time of the cultures during the exponential phase of growth was calculated from the slope of a graph of log OD650 versus time.

|  | MDS41-R13 | MG1655 |
|---|---|---|
| Stationary phase OD650, overnight seed culture | 1.92 | 2.22 |
| pH, overnight seed culture | 8.05 | 8.45 |
| Growth rate in exponential growth phase | 53 minutes | 51 minutes |
| Lag phase, MDS41-R13 versus MG1655 | 72 minutes | NA |

Electroporation of Competent E. coli Grown in LB Medium

Overnight seed cultures were prepared as described above.

From this seed culture, 500 μl was inoculated into 50 ml LB in 250 ml baffled Erlenmeyer flasks, incubated in an orbital shaker at 37° C. at 200-220 rpm and the OD650 of the culture was monitored as described above. For greater quantities of cultures, additional cultures were set up as described above and grown in parallel. When the OD650 reached the desired value, the flask was placed on ice to reduce the temperature to 0-4° C. From this point all manipulations were made at 0-4° C. All tubes and solutions were chilled before use.

1. Cultures were centrifuged in sterile 250 ml centrifuge bottles in the GSA rotor of a Sorvall RC2B or RC5B centrifuge for 10 minutes at 5,000 rpm at 4° C. to separate the E. Coli cells as a pellet.
2. Cells were suspended in 250 ml sterile MilliQ water.
3. Cells were centrifuged at 5,000 rpm for 5 min
4. Cells were suspended in 250 ml sterile MiliQ water.
5. Cells were centrifuged at 5,000 rpm for 5 min
6. Cells were suspended in 250 ml 10% or 15% glycerol
7. Cells were centrifuged at 5,000 rpm for 5 min
8. Cells were suspended in a volume of 10% or 15% glycerol approximately equal to the volume of the pellet. The OD650 of the final cell suspension was determined after 200× dilution in the microplate spectrophotometer.

9. The final cell suspensions were used fresh for electroporation, or were distributed into 40 µl aliquots in 1.5 ml Eppendorf tubes, frozen on dry ice and stored at −80° C. in a freezer until use.

Frozen cell suspensions were melted by keeping the tube in the hand, then placed on ice. DNA and 0.1 cm cuvettes were also kept on ice. 1 µl DNA (normally diluted to 10 ng/µl in TE) was added to the cells, mixed briefly, then pipetted into the cuvette. The cuvette was placed in an Eppendorf device (settings: 1800 V), and an electric pulse was applied. Cells were washed out from the cuvettes by pipetting 1 ml recovery medium up and down in the cuvette. The mixture was transferred into a test tube and placed in a shaker for 1 h at 37° C. Appropriate dilutions were then spread onto agar plates containing LB and an appropriate antibiotic for selection of the transformants. The concentration of antibody was used that suppressed the growth of the untransformed cells but not of the transformed cells.

Specific conditions used:
OD650 of culture at hervest=0.60
Transforming DNA=pUC19 10 pg/transformation
Transformed fresh
Recovery medium=LB

|  | Transformation frequency (transformants/microgram DNA) | |
| --- | --- | --- |
|  | MDS41-R13 | MG1655 |
| pUC19 | $9.3 \times 10^8$ | $4.6 \times 10^7$ |

Growth of E. coli MDS41-R13, MDS40 and MG1655 in LB Medium

The experiment was done as described above, with variations.

Specific variations in conditions used were as follows:
Seed culture—250 ml non-baffled Erlenmeyer flask
Main culture—250 ml baffled Erlenmeyer flask
Medium=LB

|  | MDS41-R13 | MDS40 | MG1655 |
| --- | --- | --- | --- |
| Stationary phase OD650 - seed culture | 0.96 | 1.34 | 2.00 |
| pH - seed culture | 8.43 | 8.81 | 8.90 |
| Doubling time in exponential phase - main culture | 33 min | 33 min | 33 min |
| Lag phase MDS41-R13 compared with MG1655 - main culture | 84 min | 95 min | — |
| Stationary phase OD650 - main culture | ND | ND | 2.22 |
| Stationary phase pH - main culture | 8.43 | 8.80 | 8.90 |

Growth of E. coli MDS41-R13 and MG1655 in Terrific Broth

The experiment was done as above, with variations. The specific variation in conditions used were as follows:
Seed culture—250 ml non-baffled Erlenmeyer flask
Main culture—250 ml baffled Erlenmeyer flask
Medium=Terrific Broth

|  | MDS41-R13 | MG1655 |
| --- | --- | --- |
| Stationary phase OD650 - seed culture | 3.97 | 3.30 |
| pH - seed culture | 5.63 | 5.45 |
| Doubling time in exponential phase - main culture | 36 min | 36 min |
| Lag phase MDS41-R13 compared with MG1655 - main culture | 0 min | — |
| Stationary phase OD650 - main culture | 6.76 | 6.28 |
| Stationary phase pH - main culture | 5.63 | 5.45 |

Electroporation of Competent E. coli MDS41-R13 and MG1655 Grown in Terrific Broth at High Cell Concentration and 37° C.

Competent cells were prepared and electroporated as described above, with the following differences:
Medium (seed and main cultures)=Terrific Broth
Stationary phase OD650 of seed culture MDS41-R13=6.06 & MG1655=5.37
Seed culture diluted 1:1000 into main culture medium
Main culture (duplicate) harvested at MDS41-R13=OD 2.17 & MG1655=2.26
Transforming DNA=pUC19 at 10 pg/transformation
Transformed fresh
Concentration of glycerol in final cell suspension=15%
Recovery medium=Terrific Broth

|  | Mean transformation efficiency (transformants/microgram DNA) | |
| --- | --- | --- |
|  | MDS41-R13 | MG1655 |
| pUC19 | $4.10 \times 10^9$ | $3.41 \times 10^7$ |

Electroporation of Competent E. coli MDS41-R13 and MG1655 Grown in Terrific Broth at High Cell Concentration and 37° C.

Competent cells were prepared and electroporated as described above, with the following differences:
Medium (seed and main cultures)=Terrific Broth
Stationary phase OD650 of seed culture MDS41-R13=6.99 & MG1655=5.67
Seed culture diluted 1:1000 into main culture medium
Main cultures (duplicate) harvested at MDS41-R13=OD 2.02 & MG1655=2.06
Concentration of glycerol in final cell suspension=15%
Transformation DNA=pUC19 at 10 pg/transformation
Transformed flesh and after freezing at −80° C.
Recovery medium=Terrific broth

|  | Mean transformation efficiency (transformants/microgram DNA) | |
| --- | --- | --- |
|  | MDS41-R13 | MG1655 |
| pUC19 transformed fresh | $1.1 \times 10^{10}$ | $1.64 \times 10^8$ |
| pUC19 transformed after freezing | $2.6 \times 10^9$ | ND |

In the above description, the present invention is described in connection with specific examples. It will be understood that the present invention is not limited to these examples, but rather is to be construed to be of spirit and scope defined by the appended claims.

TABLE 1

FIRST COMPLETED DELETIONS

| Deletion | Endpoints[a] | Size (bp) | Description[b] |
|---|---|---|---|
| MD1 | 263080, 324632 | 61553 | b0246–b0310; includes K-islands #16, 17, 18, CP4-6, eaeH |
| MD2 | 1398351, 1480278 | 81928 | b1336–b1411; includes K-island #83, Rac |
| MD3 | 2556711, 2563500 | 6790 | b2441–b2450; includes K-island #128, CP-Eut |
| MD4 | 2754180, 2789270 | 35091 | b2622–b2660; includes K-island #137, CP4-57, ileY |
| MD5 | 2064327, 2078613 | 14287 | b1994–b2008; includes K-islands #94, 95, 96, CP4-44 |
| MD6 | 3451565, 3467490 | 15926 | b3323–b3338; includes K-islands #164, 165 |
| MD7 | 2464565, 2474198 | 9634 | b2349–b2363; includes K-island #121 |
| MD8 | 1625542, 1650785 | 25244 | b1539–b1579; includes K-island #77, Qin |
| MD9 | 4494243, 4547279 | 53037 | b4271–b4320; includes K-island #225, fec operon, fim operon |
| MD10 | 3108697, 3134392 | 25696 | b2968–b2987; includes K-island #153, glc operon |
| MD11 | 1196360, 1222299 | 25940 | b1137–b1172; includes K-island #71, e14 |
| MD12 | 564278, 585331 | 21054 | b0538–b0565; includes K-island #37, DLP12 |

TABLE 2

SECOND SET OF COMPLETED DELETIONS

IS186 deletions (3)

```
keep dnaJ    14168,15298 (+)
*delete GP1  15388,20563   IS186, gef, nhaAR, IS1
  [IS186     15388,16730]
  [IS1       19796,20563]
keep rpsT    20815,21078 (−)
keep pheP    601182,602558 (+)
*delete GP2  602639,608573  ybdG, nfnB, ubdF, ybdJ, ybdK, IS186
  {IS186     607231,608573]
keep entD    608682,609311 (−)
keep glk     2506481,2507446 (−)
*delete GP3  2507650,2515969  b2389, b2390, b2391, b2392, nupC, IS186, yfeA
  [IS186     2512294,2513636]
keep alaX    2516061,2516136 (−)
```

IS2 deletions (3 not already deleted)

```
Keep yaiN    378830,379126 (−)
*delete GP4  379293,387870  yaiO, b0359, IS2, b0362, yaiP, yaiS, tauABCD
  [IS2       380484,381814]
keep hemB    387977,388984 (−)
*delete GP5  389121,399029  b0370, yaiT, IS3, yaiU, yaiV, ampH, sbmA, yaiw, yaiY, yaiZ
  [IS3       390933,392190]
keep ddlA    399053,400147 (−)
keep ygeK    2992482,2992928 (−)
*delete GP6  2992959,2996892  b2856, b2857, b2858, b2859, IS2, b2862, b2863
  [IS2       2994383,2995713]
keep glyU    2997006,2997079 (−)
keep ribB    3181829,3182482 (−)
*delete GP7  3182796,3189712  b3042, ygiL, IS2, yqiGHI (fimbral locus)
  [IS2       3184112,3185442]
keep glgS    3189755,3189955 (−)
```

IS5 deletions (6 not already deleted)

```
keep ybeJ    686062,686970 (−)
*delete GP8  687074,688268  IS5
keep lnt     688566,690104 (−)
keep tpx     1386329,1386835 (−)
*delete GP9  1386912,1396646  ycjG, ycjI, ycjY, ycgZ, mppA, ynaI, IS5, ynaJ, ydaA
  [IS5       1394068,1395262]
keep fnr     1396798,1397550 (−)
keep gnd     2097884,2099290 (−)
*delete GP10 2099418,2135739  IS5 plus entire O Antigen and Colanic Acid clusters
  [IS5       2099771,2100965]
keep yegH    2135858,2137507 (+)
keep proL    2284231,2284307 (+)
*delete GP11 2284410,2288200  yejO and IS5
  [IS5       2286939,2288133]
keep narP    2288520,2289167 (+)
keep gltF    3358811,3359575 (+)
*delete GP12         3359747,3365277 IS5 plus yhcADEF (K-island)
  [IS5       3363191,3364385]
keep yhcG    3365462,3366589 (+)
keep arsC    3647867,3648292 (+)
*delete GP13 3648921,3651343  yhis and IS5
```

TABLE 2-continued

SECOND SET OF COMPLETED DELETIONS

```
 (IS5       3640666,3650860]
keep slp    3651558,3652157 (+)
``` flagella
Region I

```
keep mviN1127062,1128597 (+)
*delete GP14    1128637,1140209 flgAMN flgBCDEFGHIJKL
keep me         1140405,1143590 (−)
```

Region II

```
keep yecT 1959975,1960484 (+)
*delete GP15    1960605,1977294 flh, che, mot, tap, tar, IS1
keep yecG 1977777,1978205 (+)
```

Regions IIIa and IIIb try deleting both in one action

```
keep sdiA 1994133,1994855 (−)
*delete Gp16    1995085,2021700 fli, plus amyA, yec and yed ORFs
keep rcsA 2021990,2022613 (+)
``` hsd region

```
keep uxuR 4552145,4552918 (+)
*delete GP17    4553059,4594581 yji ORFS, plus mcrBCD, hsdRMS, mrr, tsr
keep mdoB       4594719,4596971 (−)
```

Rhs elements

```
keep ybbP 519640,522054 (+)
*delete GP18    522062,529348 RhsD element & associated ORFs
keep ybbB 529356,530450 (−)
keep ybfA 728357,728563 (+)
*delete GP19    728616,738185 RhsC element & associated ORFs
keep ybgA 738224,738733 (+)
keep yncH 1524964,1525176 (+)
*delete GP20    1525914,1531648 RhsE element & associated ORFs
keep nhoA 1532048,1532893 (+)
keep nikR 3616219,361662 (+)
*delete GP21    3616623,3623309 RhsB element & associated ORFs #
    may need to leave something here to separate converging ORFs?
keep yhhJ 3623310,3624437 (−)
keep yibf 3758974,3759582 (−)
*delete GP22    3759620,3767868 RhsA element & associated ORFs
keep yibH 3767870,3769006 (−)
``` the rest of the IS elements

```
keep appA 1039840,1041138 (+)
*delete GP23    1041253,1049768 yccZYC (EPS), ymcDCBA (EPS?), IS1
   [IS1         1049001,1049768]
keep cspH 1050186,1050398 (−)
keep phoH 1084215,1085279 (+)
*delete GP24    1085329,1096603 ycdSRQPT (hms homologues), IS3, ymdE, ycdU
   [IS3         1093468,1094725]
keep serX 1096788,1096875 (−)
keep baeR 2162298,216302 (+)
*delete GP25    2163172,2175230 P2 remnant, IS3, gat operon
   [IS3         2168193,2169450]
keep fbaB 2175532,2176656 (−)
keep yhhX 3577399,3578436 (−)
*delete GP26    3578769,3582674 yhhYZ, IS1, yrhAB
   [IS1         3581059,3581826]
keep ggt 3582712,3584454 (−)
keep cspA 3717678,3717890 (+)
*delete GP27    3718262,3719704 IS150
   [IS150       3718262,3719704]
keep glyS 3719957,3722026 (−)
```

We claim:

1. A method of preparing an *Escherichia coli* culture for transformation at increased efficiency as compared to *E. coli* K12 MG1655, the method comprising culturing the *E. coli* to an optical density at 650 nm of at least 0.4 in a medium, wherein the *E. coli* is an multi-deletion series strain lacking bases 263080-324632, 1398351-1480278, 2556711-2563500, 2754180-2789270, 2064327-2078613, 3451565-3467490, 2464565-2474198, 1625542-1650865, 4494243-4547279, 3108697-3134392, 1196360-1222299, 564278-585331, 15388-20563, 263080-324632, 564278-585331, 602639-608573, 1398351-1480278, 2064327-2078613, 2507650-2515969, 2556711-2563500, 2754180-2789270, 379293-387870, 389121-399029, 2992959-

2996892, 3182796-3189712, 3451565-3467490, 2464565-2474198, 1625542-1650785, 4494243-4547279, 3108697-3134392, 1196360-1222299, 687074-688268, 1386912-1396646, 2099418-2135739, 2284410-2288200, 3359747-3365277, 3648921-3651343, 1128637-1140209, 1960605-1977294, 1995085-2021700, 4553059-4594581, 522062-529348, 728616-738185, 1525914-1531648, 3616623-3623309, 3759620-3767868, 1041253-1049768, 1085329-1096603, 2163172-2175230, 3578769-3582674, and 3718262-3719704 of the *E. coli* strain K12 MG1655.

2. The method of claim 1, wherein the medium is Terrific Broth.

3. The method of claim 1, wherein the culturing is done at in excess of 26° C.

4. The method of claim 1, wherein the optical density at 650 nm is at least 0.6.

5. The method of claim 1, wherein the optical density at 650 nm is at least 1.0.

6. The method of claim 1, further comprising transforming the bacteria with a foreign DNA molecule.

7. The method of claim 6, wherein the transformants recovered are in excess of $10^{10}$ transformants per microgram of introduced DNA.

* * * * *